US00PP17985P3

(12) United States Plant Patent
Moore

(10) Patent No.: US PP17,985 P3
(45) Date of Patent: Sep. 4, 2007

(54) RASPBERRY CULTIVAR 'CASCADE DAWN'

(50) Latin Name: ***Rubus ideaus* L**
Varietal Denomination: Cascade Dawn

(75) Inventor: Patrick P. Moore, Puyallup, WA (US)

(73) Assignee: Washington State University Research Foundation, Pullman, WA (US)

( * ) Notice: Subject to any disclaimer, the term of this patent is extended or adjusted under 35 U.S.C. 154(b) by 93 days.

(21) Appl. No.: 11/058,485

(22) Filed: Feb. 15, 2005

(65) Prior Publication Data

US 2006/0185043 P1 Aug. 17, 2006

(51) Int. Cl.
*A01H 5/00* (2006.01)

(52) U.S. Cl. ..... Plt./204

(58) Field of Classification Search ..... Plt./204
See application file for complete search history.

*Primary Examiner*—Kent Bell
(74) *Attorney, Agent, or Firm*—Steven J. Adamson

(57) ABSTRACT

A new and distinct cultivar of raspberry (i.e., *Rubus idaeus* L.) is provided. The cultivar has an early harvest season and forms large, medium colored, long conic, very good flavored fruit. Based on trials on root rot infested soil, the cultivar appears to exhibit good levels of tolerance to root rot.

7 Drawing Sheets

GOVERNMENT INTERESTS

The invention was made in part with Federal formula funds pursuant to the Hatch Act and was part of Project WNP00640. The United States Government has certain rights in the invention.

FIELD OF THE INVENTION

This invention relates to a new and distinct cultivar of raspberry plant with a botanical name of *Rubus ideaus* L., and the cultivar designation 'Cascade Dawn'.

BACKGROUND OF THE INVENTION

Many cultivars of raspberry plant are known. For instance, raspberry cultivars named 'Lauren', 'Encore', 'Prelude,' and 'WSU 1090' are described in U.S. Plant Pat. Nos. 10,610, 11,746, 11,747, and 14,522 respectively. The parents of the new and distinct cultivar of the present invention are WSU 991 and WSU 608.

The instant plant, 'Cascade Dawn', originated from a hand-pollinated cross of WSU 991 (non-patented), the female parent, ×WSU 608 (non-patented), the male parent, made in 1988 at Washington State University Puyallup Research and Extension Center, Puyallup Wash. WSU 991 is a yellow-fruited raspberry selection from the Washington State University breeding program and is not patented. It produces large, firm, early season fruit. WSU 608 is a red raspberry selection from the Washington State University breeding program and is not patented. WSU 608 is productive, medium sized, with weak fruiting laterals making it difficult to harvest.

SUMMARY OF THE INVENTION

'Cascade Dawn' is distinguished primarily by its early season fruit and moderate field tolerance to root rot. The fruit is long conic with a mild, well balanced flavor.

'Cascade Dawn' is distinguished from its parent WSU 991 by having red fruit, WSU 991 is a yellow fruited selection. 'Cascade Dawn' is distinguished from WSU 991 by having a greater density of spines, darker spines, longer petiolule for the distal lateral leaflet and shorter terminal petiolule on primocane leaves, more drupelets per fruit, smaller drupelets and smaller individual seed weight.

'Cascade Dawn' is distinguished from its parent WSU 608 in having larger fruit, more drupelets per fruit, smaller individual seed weight, and an earlier harvest season.

'Cascade Dawn' is distinguished from 'Cascade Delight' (patented as 'WSU 1090', U.S. Plant Pat. No. 14,522) by having an earlier fruiting season, fruit with a lower anthocyanin level, fruit that is not as firm, and the presence of a petiolule on the distal lateral leaflet of the primocane leaves over 1 mm in length.

'Cascade Dawn' is distinguished from 'Chemainus' (not patented) by having fruit with less titratable acidity and fruit with lower a anthocyanin level. 'Chemainus' is much more susceptible to root rot than 'Cascade Dawn'.

'Cascade Dawn' is distinguished from 'Malahat' (non-patented) by producing more primocanes, having longer internodes on both primocanes and floricanes, longer petiolules on both distal lateral leaflets and basal lateral leaflets of the primocane leaves, more flowers per lateral and more flowers per flowering lateral, and more drupelets per fruit. 'Malahat' is an early season cultivar, but is much more susceptible to root rot than 'Cascade Dawn'.

'Cascade Dawn' is distinguished from 'Meeker' (non-patented) by an earlier harvest season, larger fruit, higher yield on a root sites, and the presence of a petiolule on the distal lateral leaflet of the primocane leaves over 1 mm in length. 'Meeker' is much more susceptible to root rot than 'Cascade Dawn'.

'Cascade Dawn' is distinguished from 'Prelude' (U.S. Plant Pat. No. 11,747) by having a later bloom date, larger fruit, longer fruit, greater length/width ratio for the fruit, greater number of drupelets, and smaller individual seed weight.

'Cascade Dawn' is distinguished from 'Tulameen' (non-patented) by an earlier harvest season, fruit with less soluble solids, and the presence of a petiolule on the distal lateral leaflet of the primocane leaves over 1 mm in length. 'Tulameen' is much more susceptible to root rot than 'Cascade Dawn'.

'Cascade Dawn' is distinguished from 'Willamette' (non-patented) by producing more primocanes, longer internodes for both primocanes and floricanes, earlier primocane emergence, longer petiolules on both distal lateral leaflets and basal lateral leaflets of the primocane leaves, more flowers per lateral, more nodes per lateral and more flowering nodes per lateral, larger fruit, higher yields and an earlier fruiting season. 'Willamette' is much more susceptible to root rot than 'Cascade Dawn'.

BRIEF DESCRIPTION OF THE DRAWINGS

The accompanying photographs show typical specimens of the new cultivar, in color as nearly true as it is reasonably possible to make in color illustrations of this character. Photographs are intended to show morphological features of the plant.

FIG. 1 is a photograph of canes of 'Cascade Dawn' with winter color, taken Feb. 25, 2003.

FIG. 2 is a photograph of a cane of 'Cascade Dawn', taken May 23, 2003 showing the spines and the pigmented basal spots.

FIG. 3 is a photograph of a young primocane of WSU 991, one of the parents, showing sparse yellow-green spines taken Jun. 19, 2003.

FIG. 4 is a photograph of a young primocane of WSU 608, one of the parents, showing spines with pronounced basal spots taken Jun. 3, 2003.

FIG. 5 is a photograph of the upper surface of a leaf from a primocane of 'Cascade Dawn' taken Jun. 18, 2003.

FIG. 6 is a photograph of the upper surface of leaves from a primocane of 'Cascade Dawn' and both parents taken Jun. 19, 2003.

FIG. 7 is a photograph of fruit and receptacle of 'Cascade Dawn', taken Jul. 3, 2003.

DETAILED DESCRIPTION

History and Growth

The seeds resulting from the controlled hybridization of WSU 991×WSU 608 were germinated in a greenhouse during the winter of 1988–1989. Resulting seedlings were planted in the spring of 1989 at Puyallup, Wash. The seedlings fruited in 1991 and one, designated WSU 1068, was selected for its early fruit, good flavor and apparent productivity.

During 1991–1992, the original plant selection was propagated asexually in a greenhouse at Puyallup, Wash., by rooting cuttings derived from root material. A replicated planting of four replications of three plants each was established in spring 1992 at Puyallup, Wash. Subsequently, additional test plantings were established from asexually propagated plants that were propagated from root cuttings or micropropagated using meristem cultures from axillary buds of primocanes. Plantings were established in Burlington, Mt. Vernon, Puyallup, and Vancouver, Wash. All asexually propagated plants have been observed to be true to type during all asexual multiplication and the vegetative and fruit characteristics of the original plants have been maintained. Plants fruited in the second or third season of growth after planting.

Test plantings have shown this new variety to be adapted to all tested locations in western Washington. There has been no observed winter damage, but winter hardiness is unknown.

Plants of the new variety have vigorous growth with long fruiting laterals.

Measurements

When objects could be accurately measured with an 8 mm diameter measuring opening (leaves and fruit), color was measured with a Minolta Chroma Meter CR-200b, which measures color in L*, a*, b* color coordinates. Calibration was performed using a standard white plate supplied by the manufacturer. These L*, a*, b* coordinates were converted and presented in Munsell color notation. For all other color measurements, color was compared with Royal Horticultural Society Colour Chart color plates and presented as Royal Horticultural Society Colour Chart designations.

The descriptions reported herein are from specimens grown at Puyallup, Wash., unless otherwise noted.

Size

The number of canes per hill, diameter, cane length, number of nodes, internode length, and color are given in comparison to 'Malahat' and 'Willamette' in Table 1. 'Cascade Dawn' produced many canes and was very vigorous. 'Cascade Dawn' produced more primocanes than either 'Malahat' or 'Willamette'. The internode length for 'Cascade Dawn' was longer than either 'Malahat' or 'Willamette' for both primocanes and floricanes. Plants have been grown in the hill system with 10–12 canes retained per hill and the primocanes pruned to 1.2 m in winter. The following summer, fruiting plots were 180 cm tall with a width of 120 cm.

Canes

Primocane emergence for 'Cascade Dawn' occurred approximately Mar. 8, 2002 and was earlier than for 'Willamette' (non-patented), approximately Mar. 18, 2002. When the floricanes were observed Feb. 28, 2002 the canes appeared Greed Orange group (166A). The color of the bud scales were Grayed Purple group (183A). The midwinter color of canes is shown in FIG. 1. In midsummer (Jul. 22, 2002) the cane color was much greener, Yellow-Green group (145A). At about 30 cm in height the canes had 20–40 spines per cm of cane (FIG. 2). The spines are straight and pointed toward the base of the canes. There are pigmented spots at the base of the spine that are similar or slightly lighter in color as the spines. The spine color is similar to 'Malahat' and 'Willamette', Red Purple Group (59A). The spines at 20 cm were 2.6 mm long and the basal spot at the base of the spine was 2.8 mm long. The canes are glabrous.

The canes of 'Cascade Dawn' are distinct from WSU 991, by the color and frequency of spines (FIG. 3). The canes of 'Cascade Dawn' are similar to those of WSU 608 (FIG. 4).

Leaves

The upper surface of the leaves is glabrous with some pubescence at the leaf margin. The leaves are pubescent on the lower surface. The leaflets are generally flat in cross-section. The petioles are pubescent and also have spines that are similar (but smaller) to those on the canes.

Characteristics of primocane leaves are given in Table 2. The primocane leaves are pinnately compound with 5 leaflets (FIG. 5). The leaves have 2 stipules. The distal lateral leaflets and the terminal leaflet overlap slightly on some leaves and the basal lateral leaflets and the distal lateral leaflets overlap slightly on some leaves. The leaflets are doubly serrated. The leaflets are generally ovate. The tips of all leaflets are acuminate the acute. The base of the terminal leaflet is rounded to cordate. The petiolule for the basal lateral leaflet was longer than for 'Malahat', 'Willamette', and both parents. The bases are rounded and asymmetrical. The petiolule for the distal lateral leaflet was longer than WSU 991. 'Malahat', 'Willamette' and WSU 608 all had sessile leaflets with relatively symmetrical leaf bases. The presence of a petiolule over 1 mm for the distal lateral leaflet is unusual for raspberries. The upper surfaces of leaves of a primocane of 'Cascade Dawn' are compared to WSU 991 and WSU 608 in FIG. 6.

Characteristics of floricane leaves are given in Table 3. The floricane leaves have 3 leaflets that do not overlap. The leaves have 2 stipules. The leaflets are generally ovate. The leaflet tips are acuminate to acute. The leaflet base for the terminal leaflet is cordate and the lateral leaflets are rounded.

Flowers and Fruit

Fruit of this variety ripens early in the season, with the midpoint of harvest averaging July 3 for four plantings on sites where plants of other cultivars showed obvious root rot symptoms and July 6 on sites for 9 harvest seasons without obvious root rot symptoms. 'Willamette' ripened 3 days after 'Cascade Dawn'. The length of the fruiting season averaged 24 days at Puyallup, Wash. Fruit production has not been observed on primocanes. Fruit releases easily from the receptacle when the fruit is fully ripe. It does not release easily at earlier stages of maturity. The fruit is large on sites with no obvious root rot symptoms, averaging 4.1 g over the season, similar in size to 'Tulameen'. On sites with obvious root rot symptoms, the fruit averaged 3.67 g, not differing significantly from 'Meeker' and 'Willamette'.

Although variable from year to year and among locations, May 25, 2002 was the date for the first open flowers of 'Cascade Dawn' at Puyallup, Wash., and a few days after 'Prelude', May 21, 2002. Flowers of 'Willamette' opened with 'Cascade Dawn' or slightly afterward. The lateral length, number of nodes, number of flowers, flower diameter and color are given in Table 4. 'Cascade Dawn' had more flowers per lateral than 'Willamette' and 'Malahat' and more nodes and flowering nodes per lateral than 'Willamette'. 'Cascade Dawn' had more flowers per flowering node than 'Malahat'. Flower morphology is typical of most red raspberry cultivars and is not useful to identify 'Cascade Dawn'. The petals are White Group (155D), sepals Yellow-Green Group (147D) and pedicels are Yellow-Green Group (144A) and for portions of the pedicels exposed to full light Greyed-Purple Group (183A). The flowers are perfect with generally 5 sepals, 5 petals and numerous stamens (approximately 120) and pistils (approximately 135 based on the number of developed drupelets). The flowers are self-fertile. The flowering trusses are cymose in elongate clusters and at each node on the fruiting lateral the flowers are predominantly borne singly, or sometimes in clusters of two or more. The flowers have no discernable fragrance. The pedicel length, number of fruit and number of fruiting nodes are given in Table 5. The pedicel length was similar in 'Cascade Dawn', 'Malahat' and 'Willamette'. Differences between the number of flowers (Table 4) and number of fruit (Table 5) are within sampling errors.

Fruit morphological characteristics are given in Table 6. Fruit is long conic in shape (FIG. 7). The fruit weight of 'Cascade Dawn' on Jul. 3, 2002 was larger than that of 'Malahat' and 'Prelude', and also has longer fruit. The weight of the fruit early in the season on Jul. 3, 2002 (5.99 g) is much larger than the average fruit weight for the season (3.61 g for 2002 harvest of 1999 planting). The length/width ratio was 1.29, greater than 'Prelude', 0.98. The number of drupelets for 'Cascade Dawn' was much more than 'Malahat' and 'Prelude'. The weight of individual seed was significantly less than that for 'Prelude'.

Fruit of the parents of 'Cascade Dawn', WSU 991 and WSU 608, were analyzed in 1992. WSU 991 had 85.6 drupelets/fruit, with a drupelet weight of 76 mg and an average seed weight of 2.04 mg. WSU 608 had 103.5 drupelets per fruit, drupelet weight of 40.6 mg and an average seed weight of 1.74 mg. 'Cascade Dawn' has more drupelets per fruit, and smaller average seed weight than both of its parents. 'Cascade Dawn' had a smaller drupelet weight than WSU 991.

The pH, titratable acidity, soluble solids and anthocyanin concentration of processing ripe fruit are given in Table 7. Soluble solids content of 'Cascade Dawn' fruit was less than 'Tulameen', but did not differ from the other cultivars to which it was compared. The titratable acidity of 'Cascade Dawn' had the lowest value, but was only significantly different from 'Chemainus'. With the relatively low soluble solids and low titratable acidity, the flavor of 'Cascade Dawn' fruit is mild and well balanced. The anthocyanin content of 'Cascade Dawn' fruit was only significantly different from 'Cascade Delight' and 'Chemainus'.

The flavor of 'Cascade Dawn' is very pleasant and should be well suited to fresh market use. Because of the difficulty in picking fruit of 'Cascade Dawn' at the fresh market stage of maturity, most times it will be harvested at a slightly riper stage of development. This riper fruit is best suited for local (short distance) fresh market.

Fruit of 'Cascade Dawn', 'Malahat' and 'Prelude' were harvested at a fresh market stage and stored at 4° C. for 6 days and then at room temperature (approximately 20° C.) for 4 hours. Firmness and color was measured prior to storage and after storage (Table 8). Fruit at harvest of 'Cascade Dawn' and Malahat were similar in firmness and firmer than Prelude . After storage, 'Cascade Dawn' was firmer than 'Malahat' and 'Prelude'. Color of all of the cultivars was acceptable after storage.

Fruit production was measured in eight plantings at Puyallup, Vancouver and Mt. Vernon, Wash. in replicated plots that were hand harvested (Table 9). The plantings represent 13 harvest seasons. For four of the harvest seasons, there were plants of other cultivars that showed obvious root rot symptoms. For the other nine harvest seasons there were no obvious root rot symptoms. 'Meeker', 'Tulameen' and 'Willamette' were the only cultivars that were included in all of the plantings. On sites with no obvious symptoms of root rot, the yield of 'Cascade Dawn' was equivalent to 'Meeker' and had large fruit, similar in weight to 'Tulameen'. The dates of 5%, 50% and 95% of harvest are given in Table 9. The dates for the start the harvest season, the midpoint of harvest and end of the season for 'Cascade Dawn' were earlier than for the other cultivars. On the four sites with obvious symptoms of root rot, the yield of 'Cascade Dawn' was significantly greater than the other cultivars. The harvest season for 'Cascade Dawn' was earlier than for the other cultivars. 'Malahat' was included in three of the plantings with obvious symptoms of root rot. 'Malahat' did not survive in any of these plantings.

Harvest data for 'Cascade Dawn' has not been collected from a planting where its parents, WSU 991 and WSU 608, were harvested. WSU 991 was harvested in 1990 and 1991 from a 1988 planting. WSU 991 had a midpoint of harvest one day after 'Willamette' in 1990 and two days after 'Willamette' in 1991. WSU 608 was harvested from 1984 through 1987 from a 1982 planting. The midpoint of harvest averaged six days after 'Willamette' and four days before 'Meeker'. 'Cascade Dawn' with a midpoint of harvest significantly before 'Willamette' differs from both of its parents.

'Cascade Dawn' was also subjectively evaluated in plots established in 2003 that were machine harvested at Burlington, Wash. 'Cascade Dawn' machine harvested did not release from the receptacle until overripe. 'Cascade Dawn' does not appear to be suited to machine harvesting.

Disease Resistance

'Cascade Dawn' is susceptible to the large raspberry aphid (*Amphorophora agathonica*) the vector for the mosaic virus complex. It appears to be resistant to raspberry bushy dwarf virus (RBDV) via pollen transmission. In unsprayed plots, the canes had spur blight (*Didymella applanata* [Niesel] Sacc.) infections at a moderate incidence. 'Cascade Dawn' has been planted in areas with high levels of root rot (*Phytophthora fragariae* var *rubi* Wilcox & Duncan) and has survived well. 'Cascade Dawn' appears to have some field resistance to root rot.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

TABLE 1

Cane measurements taken on Jul. 22, 2002, Puyallup, Wash.

| | CASCADE DAWN | Malahat | Willamette |
|---|---|---|---|
| Primocanes | | | |
| Diameter base (mm) | 10.4a | 10.8a | 11.4a |
| Diameter 4 ft (mm) | 7.9a | 6.3a | 8.9a |
| Length (cm) | 213a | 158b | 199ab |
| Number of nodes | 35.3a | 35.0a | 36.0a |
| Internode length (cm) | 8.7a | 4.1b | 5.2b |
| Number of canes/hill | 66a | 19c | 43b |
| Cane color | 145A | 145A | 145B |
| Spine color | 59A | 59A | 59A |
| Floricanes | | | |
| Diameter base (mm) | 12.9a | 15.3a | 12.2a |
| Diameter 4 ft (mm) | 10.2a | 10.6a | 9.0a |
| Length (cm) | 163a | 169a | 165a |
| Number of nodes | 22.0a | 29.7a | 25.3a |
| Internode length (cm) | 5.0a | 3.8b | 3.4b |
| Cane color | 146B | 146B | 146B |

Three canes were measured for each clone.
[2]Royal Horticultural Society Colour Chart designations
Means within a row followed by the same letter are not significantly different at P ≦ 0.05, by Duncan's Multiple Range Test.

TABLE 2

Primocane leaves measured at 4 feet on Jun. 19, 2003, Puyallup, Wash.

| | CASCADE DAWN | Malahat | Willamette | WSU 608 | WSU 991 |
|---|---|---|---|---|---|
| Petiole length (mm) | 66.6b | 71.2b | 65.6b | 76.4b | 99.0a |
| Rachis length (mm) | 42.8b | 42.6b | 37.4b | 45.4ab | 51.6a |
| stipule length (mm) | 5.6a | 7.0a | 7.5a | 5.8a | 6.1a |
| terminal leaflet | | | | | |
| length (mm) | 88.8b | 111.6a | 80.2b | 113.8a | 111.8a |
| width (mm) | 58.2c | 77.6ab | 54.8c | 72.4b | 88a |
| petiolule length (mm) | 22.3b | 19.6bc | 14.4c | 15.1c | 33.5a |
| distal lateral leaflet | | | | | |
| length (mm) | 71.8bc | 85.2a | 65.2c | 81.6ab | 87.4a |
| width (mm) | 35.6c | 44b | 32.6c | 37.0bc | 54a |
| petiolule length (mm) | 2.4a | 0c | 0c | 0c | 1.2b |
| basal lateral leaflet | | | | | |
| length (mm) | 81.6c | 100.4ab | 80.2c | 110.6a | 97.2b |
| width (mm) | 53.2a | 69.4a | 52.0b | 66.8a | 62.8a |
| petiolule length (mm) | 14.1a | 2.2c | 3.2c | 11.6b | 4.3c |

TABLE 2-continued

Primocane leaves measured at 4 feet on Jun. 19, 2003, Puyallup, Wash.

| | CASCADE DAWN | Malahat | Willamette | WSU 608 | WSU 991 |
|---|---|---|---|---|---|
| Color | | | | | |
| upper surface of leaflet | | | | | |
| Munsell color | 6GY4/4 | 6.5GY3/3 | 6GY4/4 | 6.5GY3/3 | 3GY4/3 |
| lower surface of leaflet | | | | | |
| Munsell color | 6GY6/2 | 6.5GY5/2 | 6GY6/2 | 6GY5/2 | 6GY6/2 |

Five leaves were measured for each clone.
Means within a row followed by the same letter are not significantly different at P ≦ 0.05, by Duncan's Multiple Range Test.

TABLE 3

Floricane leaves measured at 4 feet on Jun. 19, 2003, Puyallup, Wash.

| | CASCADE DAWN | Malahat | Willamette |
|---|---|---|---|
| Petiole length (mm) | 35.8b | 66.2b | 37.4b |
| stipule length (mm) | 0.8a | 1.9a | 2.4a |
| terminal leaflet | | | |
| length (mm) | 87.4b | 85.6b | 73.6b |
| width (mm) | 56.8b | 50.8b | 49.0b |
| petiolule length (mm) | 25.2b | 20.5bc | 23.4b |
| basal lateral leaflet | | | |
| length (mm) | 73b | 69.4b | 62.4b |
| width (mm) | 40.0b | 36.2b | 32.8b |
| petiolule length (mm) | 5.0a | 1.2b | 2.1b |
| Color | | | |
| upper surface of leaflet | | | |
| Munsell color | 5.5GY3/3 | 5.5GY3/3 | 5.5GY4/4 |
| lower surface of leaflet | | | |
| Munsell color | 5GY6/2 | 5.5GY5/2 | 5GY6/2 |

| | WSU 608 | WSU 991 |
|---|---|---|
| Petiole length (mm) | 36.4b | 63.6a |
| stipule length (mm) | 0.6a | 0a |
| terminal leaflet | | |
| length (mm) | 78.2b | 125.6a |
| width (mm) | 43.0b | 94.4a |
| petiolule length (mm) | 16.6c | 36.6a |
| basal lateral leaflet | | |
| length (mm) | 64.2b | 92.6a |
| width (mm) | 31.6b | 61.2a |
| petiolule length (mm) | 2.1b | 2.8b |
| Color | | |
| upper surface of leaflet | | |
| Munsell color | 5.5GY4/3 | 5.5GY3/3 |
| lower surface of leaflet | | |
| Munsell color | 5.5GY5/2 | 5GY5/2 |

Five leaves were measured for each clone.
Means within a row followed by the same letter are not significantly different at P ≦ 0.05, by Duncan's Multiple Range Test.

TABLE 4

Flower measurements taken at 4 feet on Jul. 22, 2002, Puyallup, Wash.

| | CASCADE DAWN | Malahat | Willamette |
|---|---|---|---|
| Flower diameter | | | |
| Sepal-sepal (mm) | 23.3b | 34.3a | 26.7b |
| petal-petal (mm) | 10.3a | 10.0a | 8.7a |
| Fruiting lateral length (cm) | 57a | 49a | 46a |
| Number of flowers/lateral | 23.3a | 11.3b | 11.0b |
| Number of nodes/lateral | 18.0a | 16.0ab | 13.3b |
| Number of flowering nodes/lateral | 10.7a | 10.3a | 7.3b |
| Flowers/flowering node | 2.23a | 1.10b | 1.53ab |
| Color[z] | | | |
| petals | 155D | 155D | 155D |
| sepals | 147D | 147D | 147D |
| pedicels[y] | 144A/183A | 144A/183A | 144A/183A |

Five flowering laterals were measured for each clone.

[z]Royal Horticultural Society Colour Chart designations

[y]First value given is for base color and second value is for portions exposed to full light.

Means within a row followed by the same letter are not significantly different at P ≦ 0.05, by Duncan's Multiple Range Test.

TABLE 5

Lateral measurements taken at 4 feet on Jul. 22, 2002, Puyallup, Wash.

| | CASCADE DAWN | Malahat | Willamette |
|---|---|---|---|
| Pedicel length (mm) | 2.68a | 2.54a | 3.14a |
| Number of nodes/lateral | 16.0a | 11.4a | 12.0a |
| Number of fruit/lateral | 21.8a | 15.4a | 16.4a |
| Number of fruit per node | 1.38a | 1.35a | 1.36a |

Five fruiting laterals were measured for each clone.

Means within a row followed by the same letter are not significantly different at P ≦ 0.05, by Duncan's Multiple Range Test.

TABLE 6

Fruit morphological characteristics, red ripe fruit harvested Jul. 3, 2002, Puyallup, Wash.

| | CASCADE DAWN | Malahat | Prelude |
|---|---|---|---|
| Fruit weight (g) | 5.99a | 4.65b | 3.91b |
| Length (mm) | 28.1a | 25.5b | 20.2c |
| Width (mm) | 21.8a | 20.6a | 20.7a |
| L/W ratio | 1.29a | 1.24a | 0.98b |
| Receptacle diameter (mm) | 10a | 8.5b | 8.1b |
| Receptacle length (mm) | 21.5a | 18.4b | 13.1c |
| Drupelet length (mm) | 5.48ab | 5.86a | 5.32b |
| Drupelet width (mm) | 4.24a | 4.5a | 4.0a |
| Number of drupelets | 135.4a | 94.8b | 95.0b |
| Drupelet weight (mg) | 44.4ab | 49.2a | 41.4b |
| Total seed weight (mg) | 178a | 136b | 171a |
| Individual seed weight (mg) | 1.33b | 1.43b | 1.79a |
| Color Munsell | 3.5R3/6 | 3.5R3/6 | 3.5R3/6 |

Means within a row followed by the same letter are not significantly different at P ≦ 0.05, by Duncan's Multiple Range Test.

TABLE 7

Analysis of raspberry fruit harvested July 2003, Puyallup, Wash.

| | Soluble solids (° brix) | pH | Titratable acidity (% citric acid) | Anthocyanins (mg/g fruit) |
|---|---|---|---|---|
| CASCADE DAWN | 10.65bc | 2.69a | 0.77b | 0.38b |
| Cascade Delight | 11.50bc | 2.76a | 1.33ab | 0.63a |
| Chemainus | 10.37c | 2.41a | 1.55a | 0.58a |
| Meeker | 12.07ab | 2.70a | 0.85b | 0.46ab |
| Tulameen | 12.77a | 2.59a | 0.97ab | 0.48ab |
| Willamette | 11.20bc | 2.52a | 0.96ab | 0.54ab |

Analysis of three replications of 10 g of fruit.

Means within a row followed by the same letter are not significantly different at P ≦ 0.05, by Duncan's Multiple Range Test.

TABLE 8

Storage of fruit harvested Jul. 5, 2002, Puyallup, Wash.

| | Fruit firmness (g) | Munsell Color |
|---|---|---|
| Fruit characteristics prior to storage | | |
| CASCADE DAWN | 247a | 5R3/6 |
| Prelude | 123b | 5R3/8 |
| Malahat | 262a | 5R3/7 |
| Fruit characteristics after storage | | |
| CASCADE DAWN | 193a | 4R3/5 |
| Prelude | 81c | 4R3/6 |
| Malahat | 182b | 4R3/5 |

Twelve fruit measured for each Malahat and CASCADE DAWN and six fruit for Prelude on each date.

Fruit stored 6 days at 4 C., then room temperature (20 C.) for 4 hours.

Means within a row followed by the same letter are not significantly different at P ≦ 0.05, by Duncan's Multiple Range Test.

TABLE 9

Harvest data comparing CASCADE DAWN with three Pacific Northwest cultivars.

| | Yield (t/a) | Fruit[y] firmness (g) | Fruit rot (%) | Fruit weight (g) | Harvest season 5% |
|---|---|---|---|---|---|
| Harvest data from sites with no obvious symptoms of root rot[z]. | | | | | |
| CASCADE DAWN | 8.1a | 166a | 7.9a | 4.09a | 26-Junc |
| Meeker | 8.5a | 168a | 4.9a | 3.25b | 4-Jula |
| Tulameen | 7.7ab | 177a | 6.9a | 4.37a | 4-Jula |
| Willamette | 6.2b | 162a | 5.0a | 3.24b | 30-Junb |
| Harvest data from sites with obvious symptoms of root rot[x] | | | | | |
| CASCADE DAWN | 7.6a | 175a | 1.2a | 3.67a | 22-Junc |
| Meeker | 3.8b | 183a | 0.8a | 3.50a | 6-Jula |
| Tulameen[w] | 0.7b | 166 | 0.7 | 3.60 | 8-Jul |
| Willamette | 3.1b | 166a | 0.2a | 2.70a | 26-Junb |

| | Harvest season 50% | 95% | Length of season (d) |
|---|---|---|---|
| Harvest data from sites with no obvious symptoms of root rot[z]. | | | |
| CASCADE DAWN | 6-Julc | 20-Julc | 24ab |

TABLE 9-continued

Harvest data comparing CASCADE DAWN with three Pacific Northwest cultivars.

| | | | |
|---|---|---|---|
| Meeker | 17-Jula | 31-Jula | 26ab |
| Tulameen | 15-Jula | 31-Jula | 27a |
| Willamette | 9-Julb | 23-Julb | 23b |
| Harvest data from sites with no obvious symptoms of root rot[x] | | | |
| CASCADE DAWN | 3-Julb | 17-Julb | 25a |
| Meeker | 16-Jula | 26-Jula | 20b |
| Tulameen[w] | 17-Jul | 29-Jul | 21 |
| Willamette | 6-Julb | 17-Julb | 21b |

[z]Data from the following harvest seasons and plantings are included:
Harvests from plantings with no obvious symptom of root rot
All plantings at Puyallup, Wash. unless noted.
1994 and 1995 harvests in 1992 planting.
1997 harvest in 1995 planting.
1998 harvest in 1996 planting.
1999 and 2000 harvests in 1997 planting.
2002 and 2003 harvests in 1999 planting.

TABLE 9-continued

Harvest data comparing CASCADE DAWN with three Pacific Northwest cultivars.

2000 harvest in 1998 planting at Mt. Vernon, Wash.
[y]Firmness data not collected from Mt. Vernon, Wash. planting.
[x]Data from the following harvest seasons and plantings
Harvests from plantings with obvious symptom of root rot
1998 harvest in 1995 planting.
1999 harvest in 1996 pianting.
2003 harvest in 2000 planting.
2001 harvest in 1999 planting at Vancouver, Wash.
Only yield data collected from Vancouver planting.
[w]No plots survived in the 1995 and 2000 plantings for Tulameen.
Tulameen only included in yield analyses. Values from 1996 planning for comparison.
Means within a column followed by the same letter are not significantly different at $P \leqq 0.05$, by Duncan's Multiple Range Test.

I claim:

1. A new and distinct variety of raspberry plant, substantially as shown and described, characterized particularly by improved tolerance to root rot.

* * * * *

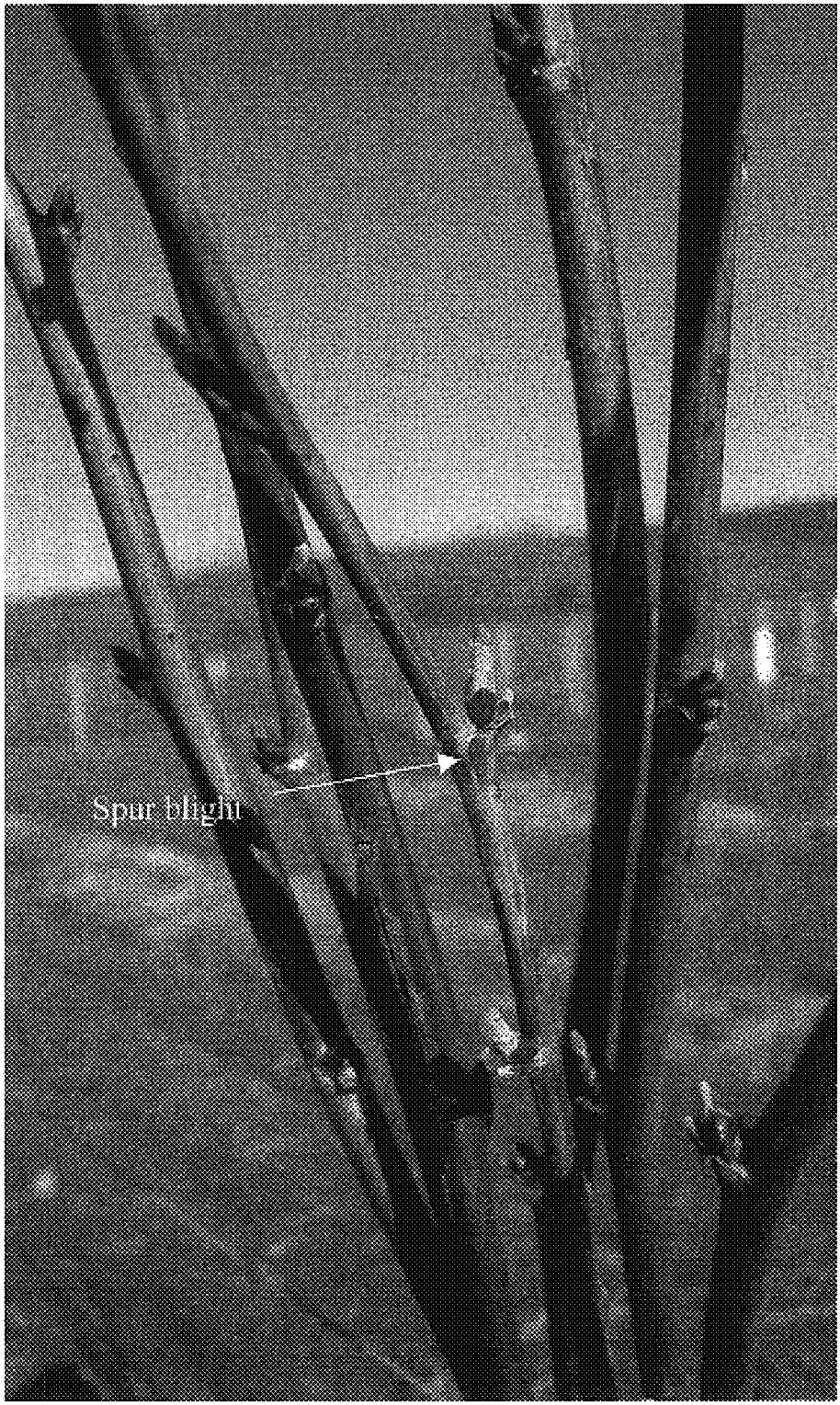
Figure 1. Canes of CASCADE DAWN with winter color, Feb 25, 2003, showing spur blight lesion.

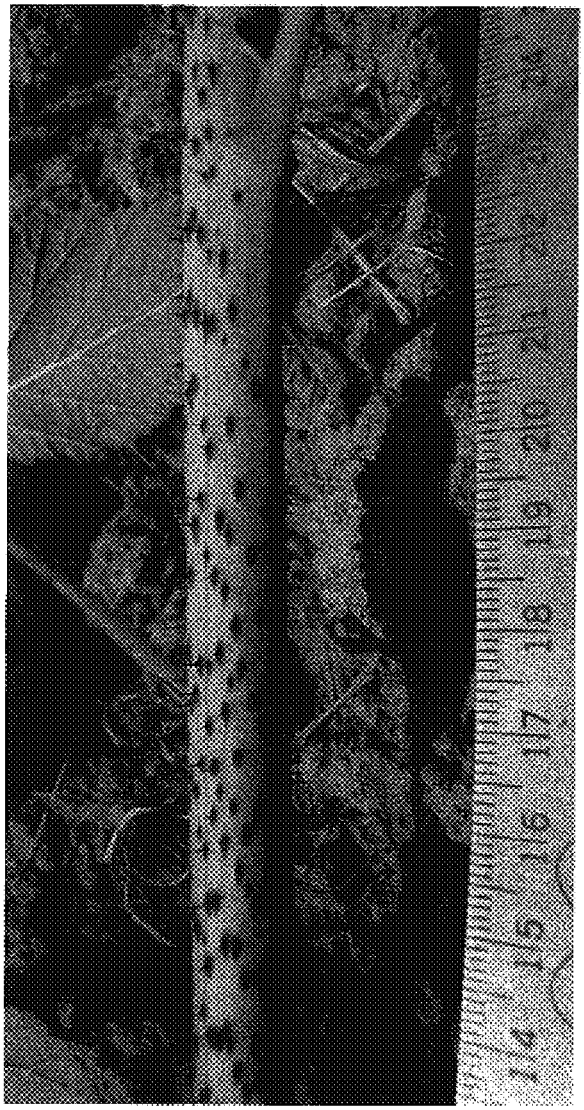
Figure 2. Cane of CASCADE DAWN showing spines and pigmented basal spots May 23, 2003, Puyallup, WA

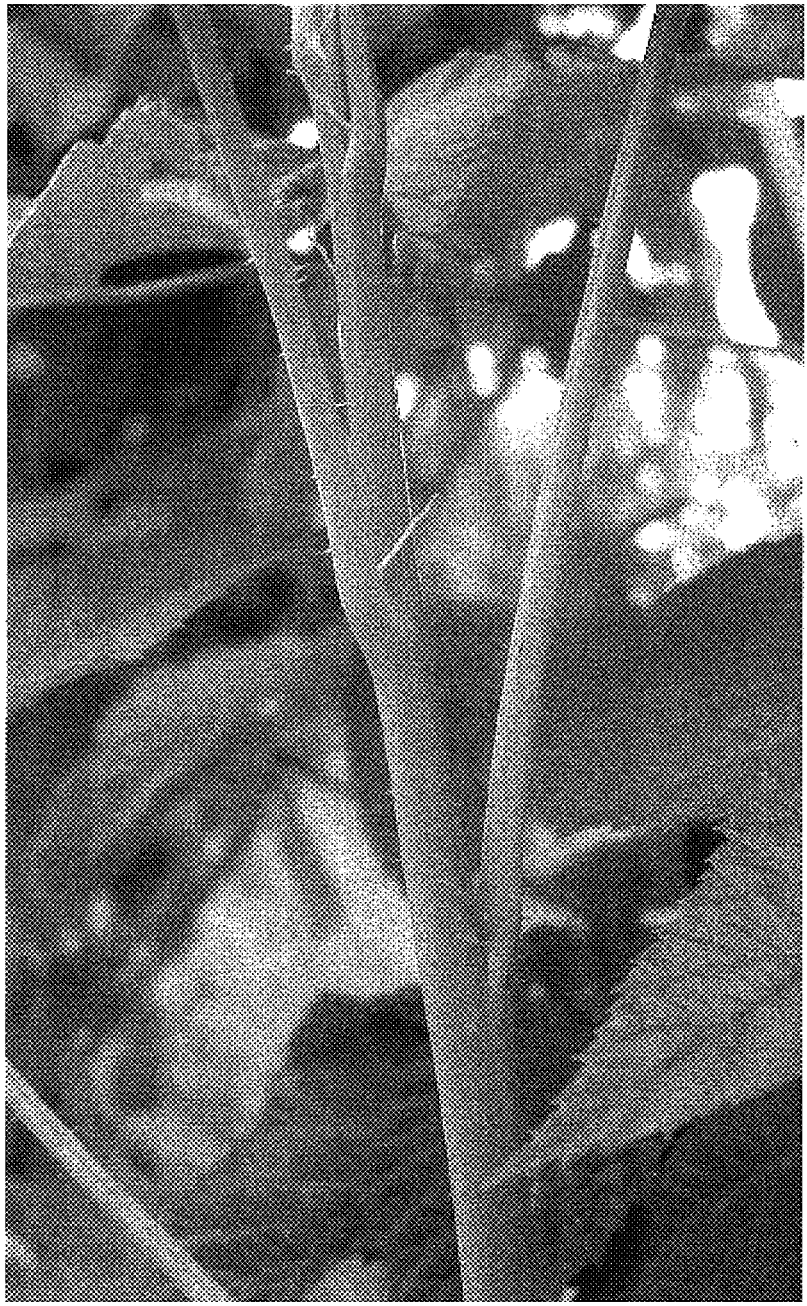
Figure 3. Cane of WSU 991 (parent), showing sparse yellow-green spines, June 19, 2003, Puyallup, WA.

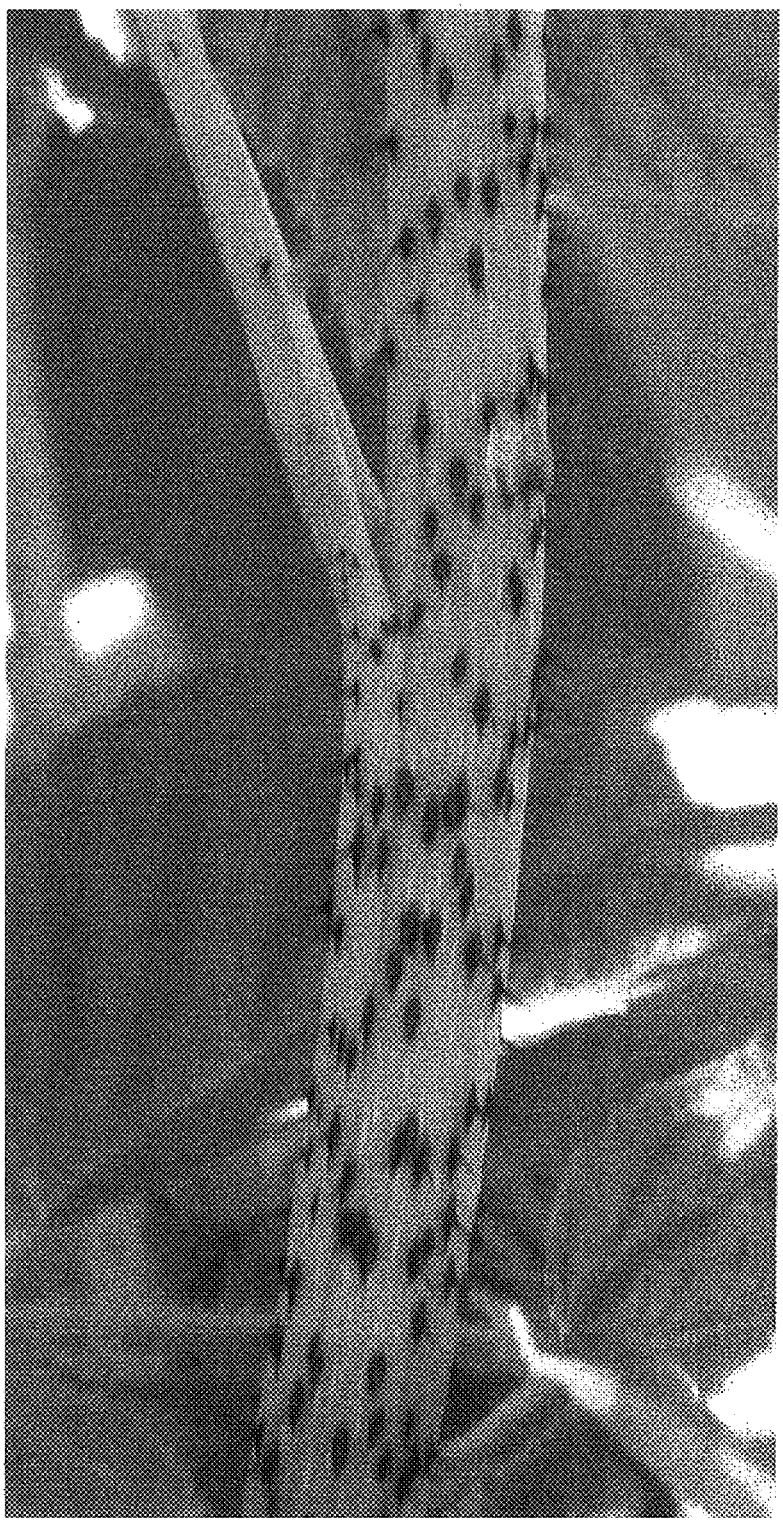
Figure 4. Cane of WSU 608 (parent) showing spines with pronounce basal spots, June 3, 2003, Puyallup, WA.

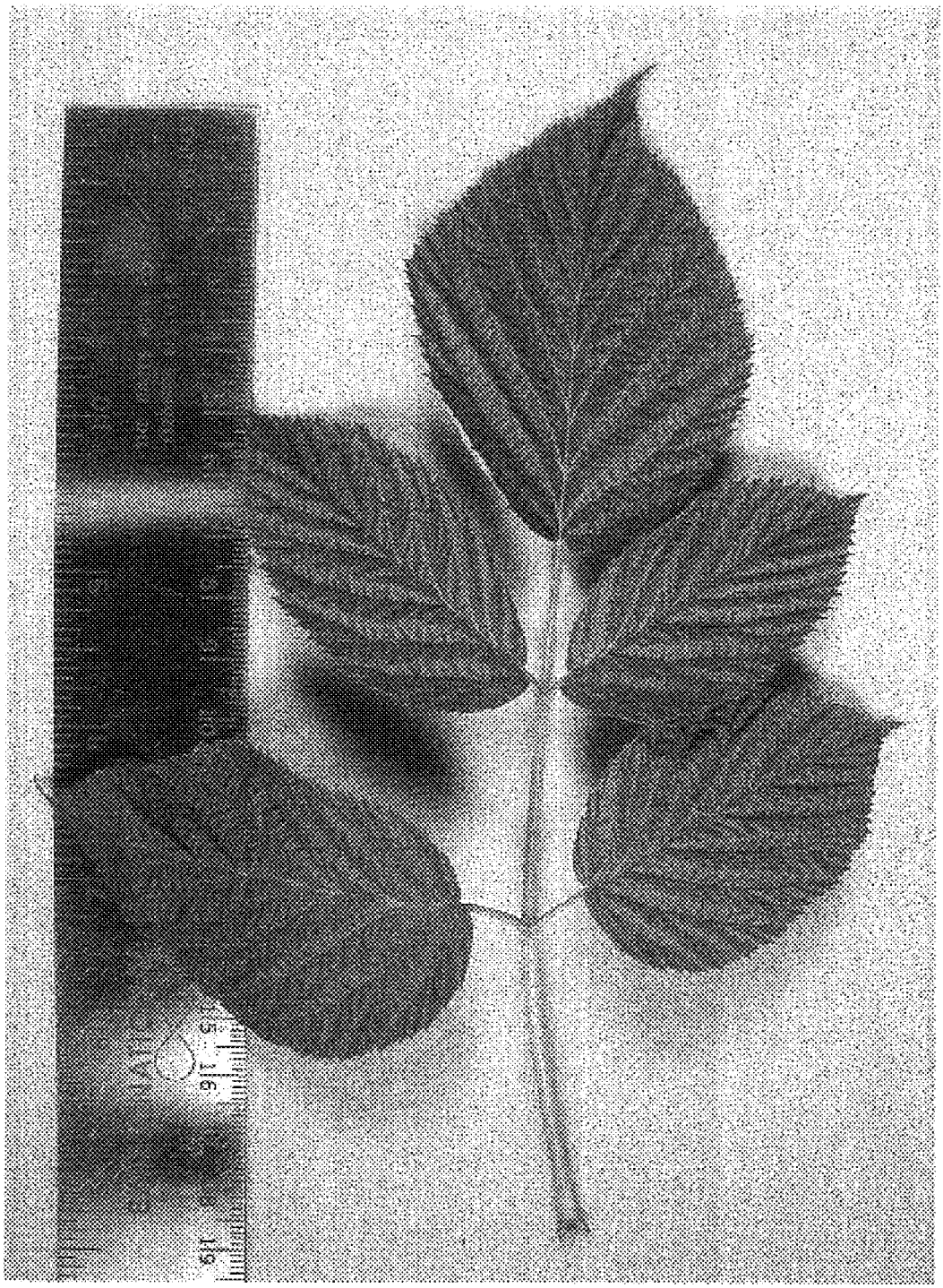
Figure 5. Leaf of CASCADE DAWN showing large petiolule for basal lateral leaflet and a petiolule for distal lateral leaflet, June 18, 2003, Puyallup, WA.

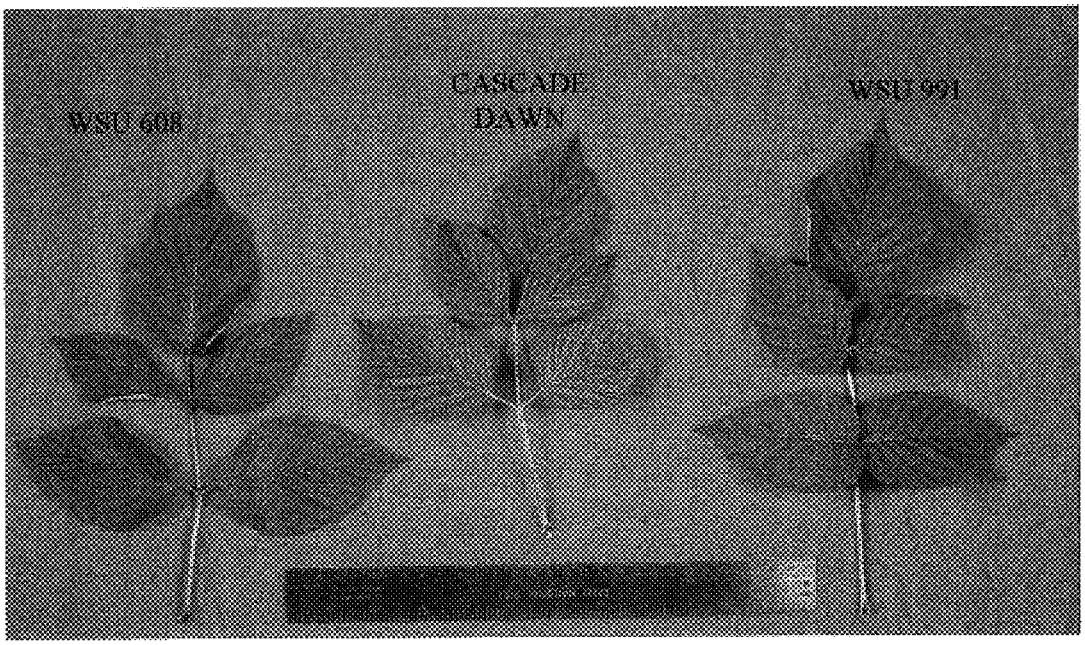
Figure 6. Primocane leaves of CASCADE DAWN and both parents, June 19, 2003.

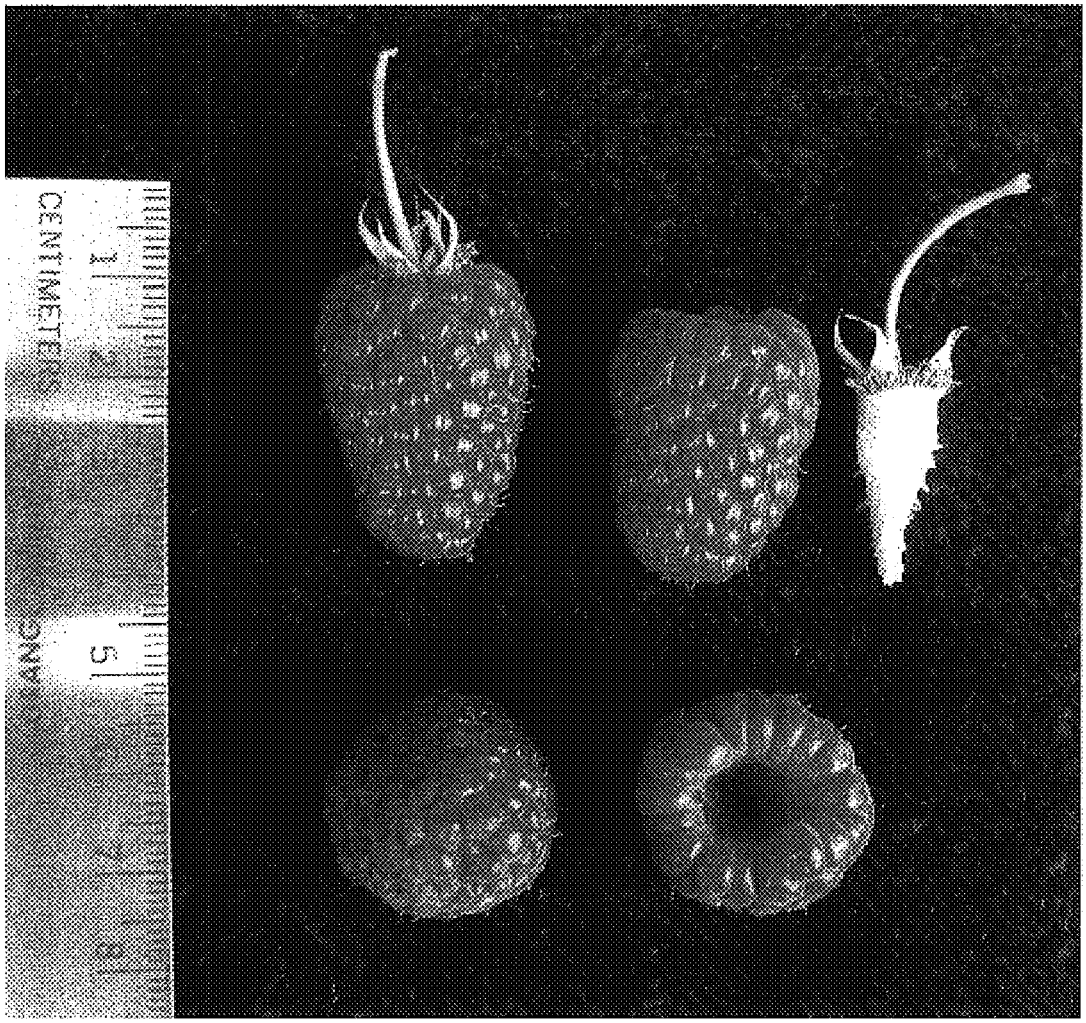
Figure 7. Fruit of CASCADE DAWN, July 3, 2002, Puyallup, WA.